United States Patent
Buhr

(10) Patent No.: US 7,238,328 B2
(45) Date of Patent: Jul. 3, 2007

(54) SOLID-STATE LIGHT SOURCE PHOTOLYTIC NITROGEN DIOXIDE CONVERTER

(75) Inventor: Martin Patrick Buhr, Golden, CO (US)

(73) Assignee: Sonoma Technology, Inc., Petaluma, CA (US)

( * ) Notice: Subject to any disclaimer, the term of this patent is extended or adjusted under 35 U.S.C. 154(b) by 426 days.

(21) Appl. No.: 10/313,827

(22) Filed: Dec. 6, 2002

(65) Prior Publication Data

US 2004/0108197 A1  Jun. 10, 2004

(51) Int. Cl.
*B01J 19/08* (2006.01)
(52) U.S. Cl. .................................... 422/186.3
(58) Field of Classification Search ............. 422/186.3
See application file for complete search history.

(56) References Cited

U.S. PATENT DOCUMENTS

| | | | |
|---|---|---|---|
| 3,840,342 A | 10/1974 | Neti et al. | |
| 3,984,688 A | 10/1976 | Von Bargen et al. | |
| 4,822,564 A | 4/1989 | Howard | |
| 5,171,610 A * | 12/1992 | Liu | 427/586 |
| 5,571,724 A | 11/1996 | Johnson | |
| 5,903,358 A | 5/1999 | Zare et al. | |
| 5,906,946 A | 5/1999 | Sausa et al. | |
| 6,280,801 B1 * | 8/2001 | Schmitt | 427/511 |
| 6,346,419 B1 | 2/2002 | Ryerson et al. | |
| 6,669,827 B2 * | 12/2003 | Austin | 204/270 |

FOREIGN PATENT DOCUMENTS

| | | |
|---|---|---|
| EP | 0 335 268 A2 | 10/1989 |
| EP | 0 511 806 A2 | 11/1992 |
| EP | 1 037 036 A1 | 9/2000 |
| FR | 2839890 A1 * | 11/2003 |

OTHER PUBLICATIONS

Ryerson et al., "An Efficient Photolysis System for Fast-Response NO2 Measurements", Journal of Geophysical Research, vol. 105, Nov. 2000, pp. 26,447-26,461.*
R.K. Stevens and J.A. Hodgeson, *Applications of Chemiluminescence Reactions to the Measurement of Air Pollutants, Anal. Chem.*, 45, p. 443A (1973.

(Continued)

*Primary Examiner*—Kishor Mayekar
(74) *Attorney, Agent, or Firm*—Patton Boggs, LLP

(57) ABSTRACT

A solid-state light source photolytic $NO_2$ converter including a reaction chamber made of a reflective material with diffuse reflective properties, whereby the reaction chamber includes a low volume gas cell wherein the gas sample residence time is less than 5 seconds is provided. The $NO_2$ in the air sample is exposed to ultraviolet radiation at wavelengths less than 420 nm, whereby the $NO_2$ is converted to NO. The NO is subsequently measured using an NO analyzer. The solid-state light source includes diode lasers and LED's that emit UV wavelength in the range of 350–420 nm. The use of a narrow wavelength range afforded by the solid-state light source results in an interference-free conversion of $NO_2$ to NO at high efficiency.

7 Claims, 5 Drawing Sheetse

OTHER PUBLICATIONS

L.P. Breitenbach and M. Shelef, Development of a Method for the Analysis of NO2 and NH3 by NO-Measuring Instruments, J. Air Poll. Control Assoc., 23, p. 128 (1973).

Kley D. and McFarland M., Chemiluminescense detector for NO and NO2, Atmospheric Technology, 12 (1980).

National Ambilent air Qiality Standards, 40 CFR 50 (1983), Measurement Principle and Calibration Procedure for the Measurement of Nitrogen Dioxide in the Atmosphere (Gas Phase Chemiluminescense).

Ryerson, et al., An efficient photolysis system for fast response NO2 measurements, Journal Geophys. Res., 105 (2000).

* cited by examiner

SOLID-STATE LIGHT SOURCE PHOTOLYTIC NITROGEN DIOXIDE CONVERTER

FIELD OF THE INVENTION

This invention generally relates to a nitrogen dioxide converter and more specifically concerns a nitrogen dioxide converter having a solid-state light source that results in interference-free conversion of $NO_2$ to NO at high efficiency and reduced operating and maintenance costs.

PROBLEM

The National Ambient Air Quality Standards (NAAQS) identify nitrogen dioxide ($NO_2$) as a health risk and limit the permissible level of $NO_2$ to 0.053 ppm (parts-per-million) in ambient air. In addition, $NO_2$ plays a central role in the photochemical production of ozone ($O_3$). For both of these reasons various methods to measure the concentration of $NO_2$ in ambient air have been developed.

The goal of these developed methods has been to achieve a high conversion efficiency of $NO_2$ to NO (nitric oxide) with minimal interferences from other reactive nitrogen species that are present in the ambient air to enable the measurement of the concentration of $NO_2$ as indicated by the corresponding concentration of NO. However, the presence of NO in the air sample due to the conversion of other reactive nitrogen species results in inaccurate readings. Interference species include $ClONO_2$ (chlorine nitrate), $N_2O_5$ (nitrogen pentoxide), $HNO_3$ (nitric acid), $HO_2NO_2$ (peroxynitric acid, PNA), $RONO_2$ (alkyl nitrates), $CH_3O_2NO_2$ (peroxyacetyl nitrate, PAN), $BrONO_2$ (bromine nitrate), $NO_3$ (nitrate radical), HONO (nitrous acid). In prior art, system interferences may arise from unwanted conversion of other ambient nitrogen-containing compounds to NO or $NO_2$ in the sample lines and photolysis cell, either by gas-phase photolysis, gas-phase thermal decomposition or surface-mediated processes (Ridley et al., 1988; Parrish et al., 1990; Gao et al., 1994; and Bradshaw et al., 1999). The EPA (Environmental Protection Agency) standard method relies on conversion of $NO_2$ to NO using a heated molybdenum catalytic converter followed by measurement of the resultant NO by chemiluminescence with ozone (Stevens and Hodgeson (1973), Breitenbach and Shelef (1973), NAAQS, 1983). This method attains high conversion efficiency but is flawed because there are several other compounds in ambient air, commonly present at concentrations equal to or greater than $NO_2$, that are also converted to NO (e.g., nitric acid ($HNO_3$) and peroxyacetyl nitrate (PAN)).

Although not part of the EPA standard method, another method to convert $NO_2$ to NO that has been described is by photolysis, wherein ultraviolet light at wavelengths between 300 and 420 nm is used to photolyze $NO_2$ to NO, followed by measurement of the resultant NO by chemiluminescence with ozone (e.g., Neti and Rocks (1974), Kley and MacFarland (1980), Ryerson, et al. (2000)). This method results in greater specificity for $NO_2$, but is hampered by relatively low conversion efficiency and detrimental effects of using the broadband light sources typically employed (e.g., high-pressure mercury lamp, xenon arc lamp, mercury arc lamp).

The detrimental effects are largely based on the broad spectrum of light applied to the sample. The sources that produce significant radiation in the infrared (>1000 nm) result in heat being added to the air sample, which in turn resulted in thermal conversion of labile compounds such as PAN and PNA. The broadband sources also emit radiation in the UV at both shorter and longer wavelengths than useful for $NO_2$ conversion, often resulting in photolytic conversion of interferent species (e.g., $HNO_3$ and the halogen nitrates at wavelengths less than 350 nm).

The relatively low conversion efficiency afforded by the conventional photolytic methods has typically been compensated for by allowing for longer residence time in the photolysis chamber. This practice further complicates the conversion by allowing for back reaction of the NO produced with ambient ozone. Ideally the photolysis would take place in one second or less to minimize the effects of the back reaction.

Another limitation of prior methods is associated with the photolysis chamber of the system. Typically the prior art either designed the chamber so that the light beam did not contact the walls of the chamber, or designed for reflective chamber walls using specular reflector. In the case of the systems that limited contact of the light beam with the walls some portion of the gas sample was not illuminated, thus limiting the efficiency of the system. In the case of the systems that used a specular reflector, typically aluminum, the reflective efficiency of the reflective surface was on the order of 0.9. Whereas 0.9 is a reasonably large reflectivity, in practice this means that 10% of the radiant energy is lost on every reflection. The result is that the energy added to the photolysis cell is rapidly lost. As mentioned above, one problem that arises from the use of broadband sources is the occurrence of spurious signals that result from photolysis of other nitrogen containing species at wavelengths produced by the source. By producing wavelengths outside the $NO_2$ quantum yield curve, these lamps photolyze other nitrogen compounds such as $ClONO_2$, $N_2O_5$, $HNO_3$ (nitric acid), $HO_2NO_2$, $CH_3ONO_2$, PAN, $BrONO_2$, $NO_3$ and HONO. To prevent the photolysis of these unwanted or spurious compounds, filters are used to narrow the emission spectrum of the broadband light source. In addition, when using a single channel system, where the light source needs to be blocked to allow for the determination of the NO species in the ambient air, the broadband light source needs to be blocked so as to not photolyze the $NO_2$. Oftentimes, a mechanical shutter is used to block the broadband light source. This adds to the number of mechanical parts involved in the testing procedure and produces a different condition of the cell in terms of heating in the NO (background—shutter closed) and $NO_x$ (shutter open) modes.

Finally, the existing photolysis-based methods have not seen widespread use because of the operating costs associated with replacement of the relatively short-lived light sources (typically 200–1500 hours of continuous operation depending on the lamp, with costs ranging from $200–$900 per lamp). Replacing these lamps also equates to man hours spent and instrument downtime incurred, both added costs to the testing procedure. In addition to these costs, additional costs of prior methods include the mechanical shuttering devices, filters, broadband light source power requirements and elaborate positioning devices employed to position the broadband light source.

Information relevant to attempts to address these problems can be found in U.S. Pat. Nos. 3,840,342 issued Oct. 8, 1974 to Neti et al.; 6,346,419 issued Feb. 12, 2002 to Ryerson. However, each one of these references suffers from one or more of the following disadvantages: non-specific wavelength emissions, lack of photon residence time, cost and efficiency.

SOLUTION

The above-described problems are solved and a technical advance achieved by the solid-state light source photolytic nitrogen dioxide converter which generates a narrow band of light emissions that are emitted within a reaction chamber that comprises a diffuse reflector, thereby creating a reaction chamber with a high concentration of wavelength-specific photons to increase the efficiency and specificity of the reaction chamber to convert photoreactive compounds. Additionally, the use of a solid-state light source eliminates the need and expense of filters used with broadband light sources. Further, the need and expense for mechanical shutters for single channel systems that employ broadband light sources is eliminated as well.

The invention described herein relies on the use of solid-state light sources to perform a photolytic conversion of photoreactive compounds such as $NO_2$ to NO. The narrow emission band of the solid-state light sources provides an efficient conversion with minimal or no interferences. The lack of interferences results from the narrow wavelength range of light produced by the source and the lack of sample heating by the source. The various embodiments of the invention, including both different light sources and photolysis chambers, allow for a high efficiency in photoreactive compound conversion in a short photolysis period (ca. one second). The solid-state light sources demonstrated for this application include both a diode laser and light-emitting diodes (LED's) emitting at photochemical reactive wavelengths. Solid-state light source means a diode in which a semiconductor material produces either the spectrally coherent output beam (diode laser), or a narrow range of wavelengths (LED—typically full width at half maximum=20 nm).

The solid-state light source photolytic nitrogen dioxide converter produces an increased amount of wavelength-specific photons in the reaction chamber at one time, which is done using the diffuse reflector chamber of the current invention versus a specular reflector such as aluminum foil, etc. of the prior art methods. Further, the solid-state light source is capable of being instantly turned off and on, thereby eliminating the need for mechanically operated shutters and filters, which decreases the cost and improves the reliability of the solid-state light source photolytic nitrogen dioxide converter. In addition, the increased lifetime of the solid-state light sources (typically 5000-10000 hours) over broadband light sources further decreases the cost and maintenance associated with changing the broadband light sources employed in prior art methods and enhances the attractiveness of this apparatus.

The invention provides a photolytic $NO_2$ converter for converting $NO_2$ present in a gas sample into NO comprising: a body including a reaction chamber located substantially within the body, the reaction chamber possessing at least one aperture; a reaction chamber inlet in communication with the reaction chamber for transporting a gas sample into the reaction chamber; a reaction chamber outlet in communication with the reaction chamber for transmitting a processed gas sample out of the reaction chamber; and at least one solid-state light source, located substantially adjacent to the at least one aperture to enable UV wavelength radiation to pass from the at least one solid-state light source into the reaction chamber through the at least one aperture, for converting $NO_2$ present in a gas sample transported into the reaction chamber by the reaction chamber inlet into NO in a processed gas sample for transportation out of said reaction chamber by the reaction chamber outlet.

Preferably, the photolytic $NO_2$ converter further includes NO detector means, in communication with the reaction chamber outlet, for generating a signal indicative of a concentration of NO in the processed gas sample. Preferably, the photolytic $NO_2$ converter further includes at least one heat sink mounted to the body and located substantially near the at least one solid-state light source. Preferably, the photolytic $NO_2$ converter further includes at least one thermoelectric cooling device mounted to the body and located substantially near the at least one solid-state light source. Preferably, the reaction chamber comprises a reflective material. Preferably, the reflective material possesses diffuse reflective properties. Preferably, the reflective material possesses specular reflective properties.

Preferably, the reflective material is selected from the group consisting of Teflon™-based materials and Barium Sulfate. Preferably, the reflective material is selected from the group consisting of aluminum and silver. Preferably, the solid-state light source is UV wavelength light emitting diodes (LED's). Preferably, the solid-state light source is a UV wavelength diode laser. Preferably, the UV wavelength is between 350 and 420 nm. Preferably, the photolytic $NO_2$ converter further includes a means for controllably introducing the gas sample to the reaction chamber, the reaction chamber, and the means for controllably introducing the gas sample from the reaction chamber, each comprises a volume which minimizes a residence time of the gas sample in the photolytic $NO_2$ converter.

In another aspect the invention provides a photolytic $NO_2$ converter for converting $NO_2$ present in a gas sample into NO, comprising: a body including a reaction chamber located substantially within the body, the reaction chamber made of Teflon™-based material and possessing at least one aperture; a reaction chamber inlet in communication with the reaction chamber for transporting a gas sample into the reaction chamber; a reaction chamber outlet in communication with the reaction chamber for transmitting a processed gas sample out of the reaction chamber; and at least one LED capable of producing UV wavelength radiation in the range of 350–420 nm, located substantially adjacent to the at least one aperture to enable UV wavelength radiation to pass from the at least one LED into the reaction chamber through the at least one aperture, for converting $NO_2$ present in a gas sample transported into the reaction chamber by the reaction chamber inlet into NO in a processed gas sample for transportation out of the reaction chamber by the reaction chamber outlet.

Numerous other features, objects and advantages of the invention will become apparent from the following description when read in conjunction with the accompanying drawings.

DETAILED DESCRIPTION

Figure 1:
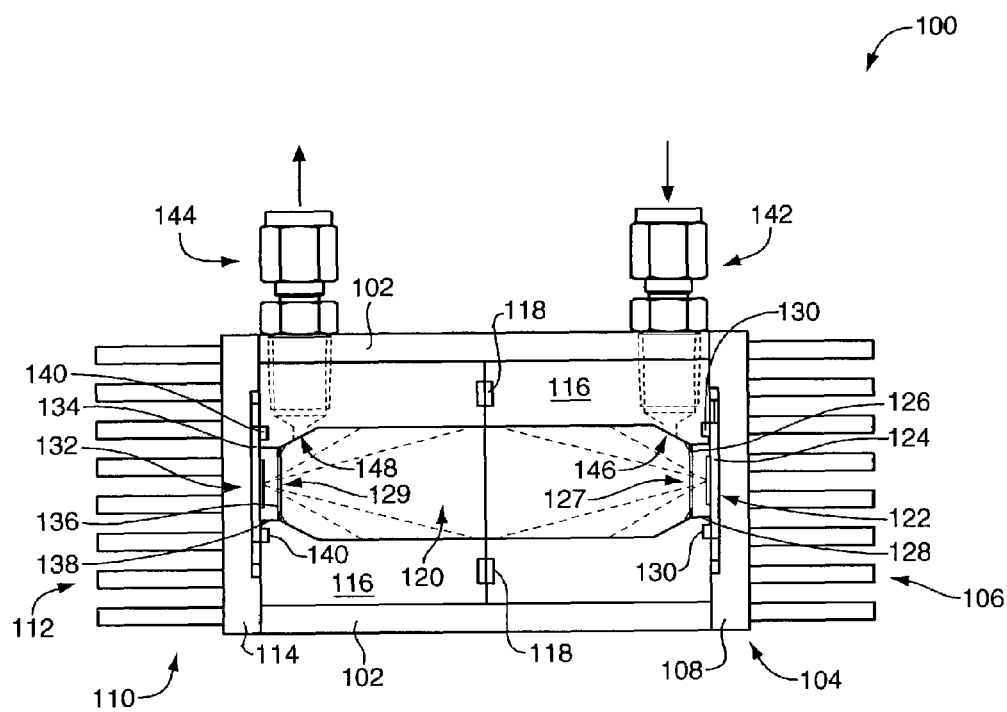
FIG. 1 illustrates a cross-section view of an embodiment of the solid-state light source photolytic nitrogen dioxide converter including LED's.

In general, $NO_2$ is photodissociated at ultraviolet (UV) wavelengths below 420 nm in the following first order process, $$NO_2 + h\nu \rightarrow NO + O \quad (1)$$

with the rate constant for photolysis given by j (units of $s^{-1}$), which is the wavelength-integrated product of the photon flux (photons $cm^{-2}s^{-1}$), the weakly temperature-dependent $NO_2$ absorption cross-section ($cm^2$ $molecule^{-1}$), and the quantum yield for photodissociation (molecules $photon^{-1}$) (DeMore, W. B., et al., Chemical Kinetics and Photochemical Data for use in Stratospheric Modeling, NASA Jet Propulsion Laboratory, Pasadena, Calif., 1997). In air, the O atom formed in formula (1) reacts rapidly with molecular oxygen ($O_2$) to form $O_3$, $$O + O_2 \rightarrow O_3 \quad (2)$$

which can then react with NO to re-form $NO_2$, $$NO + O_3 \rightarrow NO_2^* + O_2 \quad (3)$$

where $NO_2^*$ equals electronically excited $NO_2$. The $NO_2^*$ is then relaxes by the energy given off in formula (4), $$NO_2^* \rightarrow NO_2 + h\nu \quad (4)$$

Efficient conversion of $NO_2$ to NO serves to maximize that difference and improve instrumental sensitivity for $NO_2$. Reaction (4) is used in the chemiluminescence measurement to determine the resulting product NO, which is measured as an increase in chemiluminescence above that from ambient NO when mixed with percent levels of $O_3$.

UV means ultraviolet radiation in the region of electromagnetic spectrum including wavelengths from 40 to 4000 Å (4 to 400 nm). Chemiluminescence means the emission of absorbed energy (as light) due to a chemical reaction of the components of the system. Chemiluminescence occurs in thousands of chemical reactions covering a wide variety of compounds, both organic and inorganic.

Quantum yield for a photochemical reaction means the number of moles of a stated reactant disappearing, or the number of moles of a stated product produced, per unit of light of the stated wavelength absorbed. Quantum yield also means the number of photon-induced reactions of a specified type per photon absorbed. Photolytic and photolysis means the use of radiant energy to produce chemical changes. Photolytic and photolysis also means decomposition of a compound into simpler units as a result of absorbing one or more quanta of radiation. Absorption cross-section means the ratio of the amount of power removed from a beam by absorption of radio energy by a target to the power in the beam incident upon the target.

In a single channel system in the prior art means that a sample of gas is first subjected to photolysis wherein the $NO_2$ is converted to NO and any original NO in the gas sample in combination with the photolysed $NO_2$ to NO is analyzed by an NO detector. Then the broadband light source is blocked by a mechanical shutter, so that the $NO_2$ in the original gas sample is not converted to NO and then the gas sample is analyzed by cheminluminescence to detect only the NO in the original sample. This second NO reading is subtracted from the first reading to give a $NO_2$ determination in the original sample. Only one reaction chamber is employed in this analysis and therefore it is called a single-channel photolysis system.

In a dual-channel photolysis system, which includes two detector channels, sample residence times are made identical by including a cell, equal in volume to the photoloysis cell but not illuminated, in the channel flow path. This configuration permits simple and accurate retrieval of ambient $NO_2$ at high time resolution. While the NO channel time response is degraded relative to that obtained with no added volume, the degradation is minimal in the present design. Residence time means the average length of time a particle of reactant spends within a process vessel or in contact with a catalyst.

FIG. 1 illustrates the preferred embodiment of the solid-state light source photolytic nitrogen dioxide converter 100 which includes a body 102. Solid-state means pertaining to a circuit, device, or system that depends on some combination of electrical, magnetic, and optical phenomena within a solid that is usually a crystalline semiconductor material. Body 102 is made of a rigid or semi-rigid material such as aluminum. First heat sink 104 is attached to the body 102 and includes a multiplicity of first heat sink pins 106 and a first heat sink base 108. The first heat sink 104 is attached to the body 102 by screws, or alternatively by other fasteners such as bolts, clamps, couplings or pins. A second heat sink 110 is attached to the body 102. The second heat sink 110 includes a multiplicity of second heat sink pins 112 and a second heat sink base 114.

The heat sinks 104, 110 and body 102 are comprised of a material with good heat transfer properties, such as aluminum. The heat sinks 104 and 110 are attached to the body 102 by screws, or alternatively by other fasteners such as bolts, clamps, couplings or pins. The preferred embodiment 100 employs two heat sinks 104 and 110, but any number of heat sinks 104, 110 can be employed as described above.

The body 102 encloses a reflective material 116 which defines the reaction chamber 120. In the preferred embodiment, the reflective material 116 is comprised of a material with diffuse reflector properties, such as Teflon™. Diffuse reflector means any surface whose irregularities are so large compared to the wavelength of the incident radiation that the reflected rays are sent back in a multiplicity of directions. Teflon™ means polytetrafluoroethylene (PTFE) fluorocarbon polymers available as molding and extrusion powders, aqueous dispersion, film, finishes, and multifilament yarn or fiber. The reflective material 116 can be milled in one piece or two as shown in FIG. 1. If the reflective material 116 is milled in two pieces, then preferably an o-ring groove 118 is milled to accept an o-ring (not shown) to make a gas-tight seal between the two pieces of reflective material 116.

Although the reflective material 116 of the preferred embodiment is made of material with diffuse reflector properties, in another aspect of the present invention, it could be made of a different diffuse reflector (e.g., barium sulfate ($BaSO_4$) coated on the outside of a glass cylinder or a material with specular reflector properties such as aluminum foil. Specular reflector means a reflecting surface (polished metal or silvered glass) that gives a direct image of the source, with the angle of reflection equal to the angle of incidence. A specular reflector is also known as regular reflector or specular surface and it produces a direct reflection, mirror reflection or regular reflection.

In the preferred embodiment 100, reaction chamber 120 is formed in the shape of a cylinder within the reflective material 116. The reaction chamber 120 further include tapered ends toward the distal ends of the reaction chamber 120, however, this is not a specific limitation of the preferred embodiment 100 and the reaction chamber 120 could be shaped in other forms to allow gas passage through the reaction chamber 120. All or most of the surface of the reaction chamber 120 is comprised of the reflective material 116 as described above.

A first LED module 122 is located between the first heat sink 104 and the reaction chamber 120. The first LED module 122 includes a first LED array 124, which is an array of one or more LED die. In the preferred embodiment 100, there are 60 individual LED die in the first LED array 124. LED is an acronym for light emitting diodes, which means a semiconductor diode that converts electric energy efficiently into spontaneous and non-coherent electromagnetic radiation by electroluminescence at a forward-biased pn junction. The UV radiation emitted by the first LED array 124 is represented by dotted lines within the reaction chamber 120. First LED module 122 also includes a first LED window 126 which allows the UV radiation from the first LED array 124 to enter the reaction chamber 120. The reaction chamber 120 also includes a first aperture 127 and a second aperture 129. The apertures 127 and 129 are holes in the reaction chamber 120 that allows UV radiation to pass from the solid-state light source into the reaction chamber 120. The first LED window 126 is held in place by a first LED enclosure 128. The first LED module 122 also includes a first LED module o-ring groove 130 that accepts an o-ring (not shown) to create a gas-tight seal between the first LED module 122 and the reaction chamber 120.

A second LED module 132 is located between the second heat sink 110 and the reaction chamber 120. The second LED module 132 includes a second LED array 134, which is an array of one or more LED dies. In the preferred embodiment 100, there are 60 individual LED die in the second LED array 134. The UV radiation emitted by the second LED array 134 is represented by dotted lines within the reaction chamber 120. Second LED module 132 also includes a second LED window 136 which allows the UV radiation from the second LED array 134 to enter the reaction chamber 120. The second LED window 136 is held in place by a second LED enclosure 138. The second LED module 132 also includes a second LED module o-ring groove 140 that accepts an o-ring (not shown) to create a gas-tight seal between the second LED module 132 and the reaction chamber 120. The LED enclosures 128 and 138 are made of a non-reactive material that will not absorb photons, such as gold plated aluminum. The LED windows 126 and 136 are made of a material that is transparent to UV radiation, such as quartz glass.

The light paths of the UV radiation may be axial or orthogonal relative to the reaction chamber 120. Axial light path means located on, around or along an axis. Orthogonal light path means perpendicular or some concept analogous to it.

The solid-state light source photolytic nitrogen dioxide converter 100 also includes an inlet piping 142 and an outlet piping 144. The piping 142 and 144 are made of stainless steel tubing and coupling or other non-reactive material so as to not contaminate the gas sample that is transported through them. The piping 142 and 144 are attached directly to the reaction chamber 120, via threads or other fasteners, such as clips or screws.

The reaction chamber 120 includes a reaction chamber inlet 146 and reaction chamber outlet 148. Gas samples flow through the inlet piping 142 and then through the reaction chamber inlet 146 into the reaction chamber 120 where the gas sample is bombarded with UV radiation produced by the LED modules 122 and 132 and diffusely reflected by the reflective material 116, where the $NO_2$ in the gas sample is photodissociated to NO and then travels out reaction chamber outlet 148 and through outlet piping 144 to a chemiluminescence detector or laser-induced fluorescence detector as is commonly known in the prior art.

In another embodiment of the solid-state light source photolytic nitrogen dioxide converter 100, the solid-state light source is either a diode laser or the LED modules 122 and 132. In this embodiment, the solid-state light source is cooled by thermoelectric cooling devices in addition to the heat sinks 104 and 110. In this embodiment, the same reflective material 116 is used to scatter the UV radiation produced by the diode laser that creates an efficient conversion of $NO_2$ to NO in the reaction chamber 120. Thermoelectric cooling means cooling of a chamber based on the Peltier effect, where typically an electric current is sent through a thermocouple whose cold junction is thermally coupled to the cooled chamber, while the hot junction dissipates heat to the surroundings. Thermoelectric cooling is also known as thermoelectric refrigeration.

Figure 3:
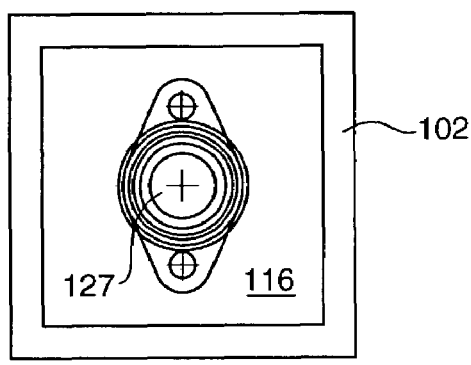
FIG. 3 illustrates an end view of the reaction chamber.

FIG. 3 is an illustration of an end view of the reaction chamber 120 in the preferred embodiment 100. This end view is of either end of the reaction chamber 120 with the heat sinks 104 and 110 removed. This view is looking axially through the reaction chamber 120. FIG. 3 also shows the first aperture 127 of the reaction chamber 120. The reaction chamber 120 may include one or more apertures 127 and 129. The apertures are cut through the reflective material 116 that comprises the reaction chamber 120 and allows UV wavelength radiation from the solid-state light source to emit through the apertures 127 and 129 into the reaction chamber.

Figure 4:
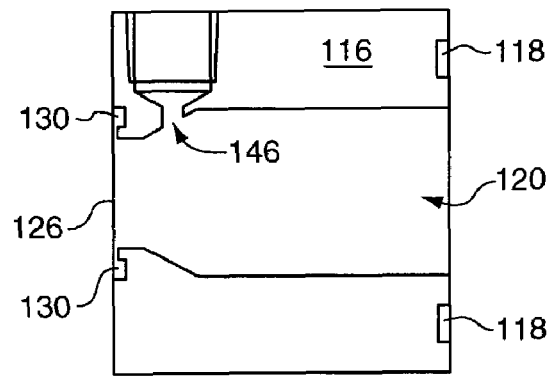
FIG. 4 illustrates a cross-section view of one end the reaction chamber.
Figure 5:
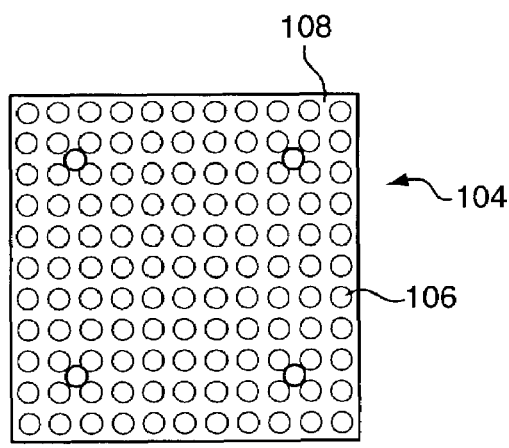
FIG. 5 illustrates the end view of a heat sink.
Figure 6:
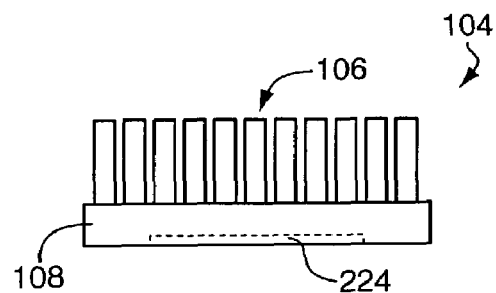
FIG. 6 illustrates a side view of a heat sink.

FIG. 4 is an illustration of a cross-section view of one end of the reaction chamber 120. FIG. 5 is an illustration of the end view of first heat sink 104. The multiplicity of the first heat sink pins 106 are shown. Though the first heat sink 104 is shown, the arrangement and multiplicity of heat sink pins would be the same on the second heat sink 110. FIG. 6 is an illustration of a side view of first heat sink 104. In the preferred embodiment, a first heat sink cut-out 224 is formed into the first heat sink 104 to allow for the first LED module 122 to fit in the first heat sink cut-out 224 and be flush with the edge of the first heat sink base 108. Though the first heat sink 104 is shown, the cut-out and arrangement of the second LED module 132 and the second heat sink base 114 would be similar as that depicted in FIG. 6.

Figure 7:
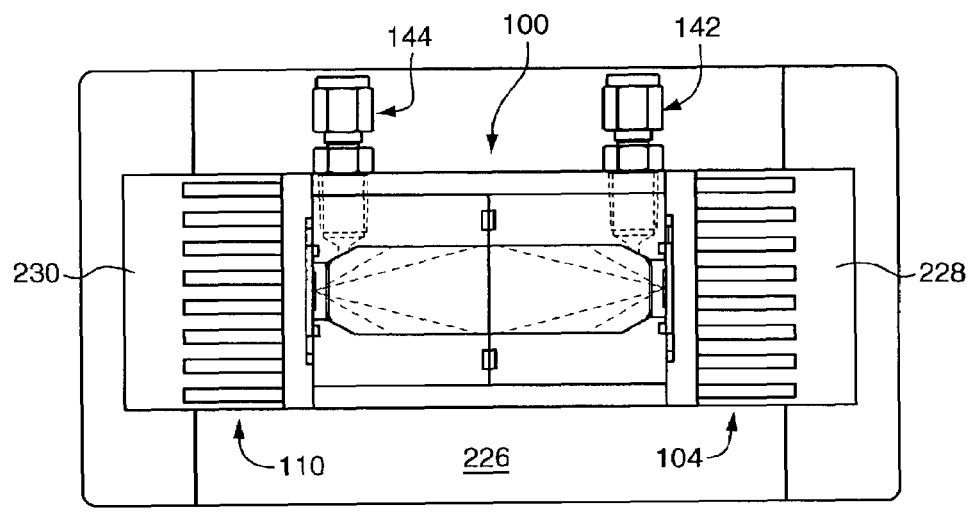
FIG. 7 illustrates a top view of the solid-state light source photolytic nitrogen dioxide converter attached to a mounting frame.
Figure 8:
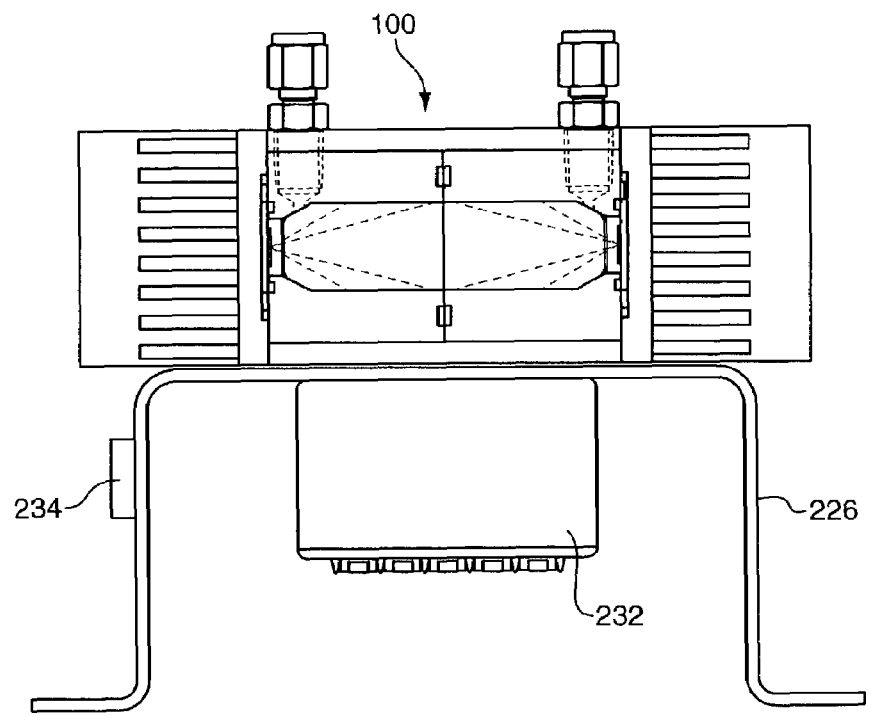
FIG. 8 illustrates a side view of the solid-state light source photolytic nitrogen dioxide converter attached to a mounting frame including a power source.

FIG. 7 is an illustration of a top view of the solid-state light source photolytic nitrogen dioxide converter 100 attached to an optional mounting frame 226. Mounting frame 226 enable the solid-state light source photolytic nitrogen dioxide converter 100 to be quickly and accurately attached and detached from existing $NO_2$ converter footprints presently in use in conventional methods. The mounting frame 226 can be made of aluminum or other rigid materials. A first heat sink fan 228 is shown attached distally from the first heat sink 104. A second heat sink fan 230 is shown attached distally from the second heat sink 110. The heat sink fans 228 and 230 are electrically powered and are commonly known to those skilled in the art. FIG. 8 is an illustration of a side view of the solid-state light source photolytic nitrogen dioxide converter 100 attached to the mounting frame 226 including a power supply 232 and power switch 234. Power supply 232 delivers electrical power to the heat sink fans 228 and 230 and LED modules 122 and 132. Power switch 234 switches the electrical power on and off to the heat sink fans 228 and 230 and LED modules 122 and 132.

Figure 2:
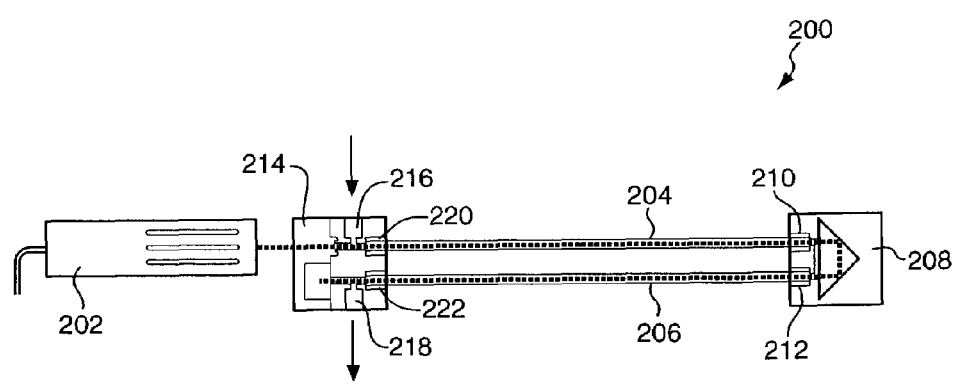
FIG. 2 illustrates a cross-section view of another embodiment of the solid-state light source photolytic nitrogen dioxide converter including a diode laser.

FIG. 2 illustrates another embodiment 200 of the solid-state light source photolytic nitrogen dioxide converter which includes a diode laser 202. Laser means a device that produces a beam of coherent or monochromatic light as a result of photon-stimulated emission. Such beams have extremely high energy, because they consist of a single wavelength and frequency. Laser is an acronym for light amplification by stimulated emission of radiation. Laser diode includes a semiconductor laser which means a laser in which stimulated emission of coherent light occurs at a pn junction when electrons and holes are driven into the junction by carrier injection, electron-beam excitation, impact ionization, optical excitation, or other means. Also known as a diode laser.

The diode laser 202 includes a thermoelectric cooling device (not shown) that is commonly known to those skilled in the art. The solid-state light source photolytic nitrogen dioxide converter 200 also includes a first reaction tube 204 and a second reaction tube 206. The reaction tubes 204 and 206 are small inner diameter (I.D.) glass tubing that are the photolysis cell for the $NO_2$ reaction to NO with typically an I.D. between 0.5 to 50 mm. A prism 208 is used to direct the UV radiation from the first reaction tube 204 to the second reaction tube 206. The prism 208 is made of a material such as glass that is coated with an anti-reflective coating commonly known to those skilled in the art. Prism 208 is employed in this embodiment 200 to allow manipulation of the position of the laser beam with high throughput.

The first reaction tube 204 is sealed in the prism 208 at the prism inlet seal 210 by an o-ring (not shown) that creates a gas-tight seal. The second reaction tube 206 is sealed in the prism 208 at the prism outlet seal 212 by an o-ring (not shown) that creates a gas-tight seal. The embodiment 200 also includes block 214 for sealing the reaction tubes 204 and 206. The block 214 is made of a material such as aluminum that is coated with Teflon™. The first reaction tube 204 is attached to the block 214 by an o-ring (not shown) that creates a gas-tight seal. Further, the second reaction tube 206 is attached to the block 214 by an o-ring (not shown) that creates a gas-tight seal.

The solid-state light source photolytic nitrogen dioxide converter 200 includes a block inlet 216 that allows a gas sample to enter the block 214 and first reaction tube 204. The first reaction tube 204 is attached to the block 214 by the first reaction tube seal 220 that includes an o-ring (not shown) creating a gas-tight seal. The second reaction tube 206 is attached to the block 214 by the second reaction tube seal 222 that includes an o-ring (not shown). Tubing or piping as described above or as is commonly known to those skilled in the art is used to direct the gas sample into the block 214. The solid-state light source photolytic nitrogen dioxide converter 200 also includes a block outlet 218 that allows the gas sample to exit the second reaction tube 206 and block 214. Any number of reaction tubes 204 and 206 prisms 208 may be used in this embodiment. For example, four reaction tubes with three prisms 208 could be used in this embodiment.

Figure 9:
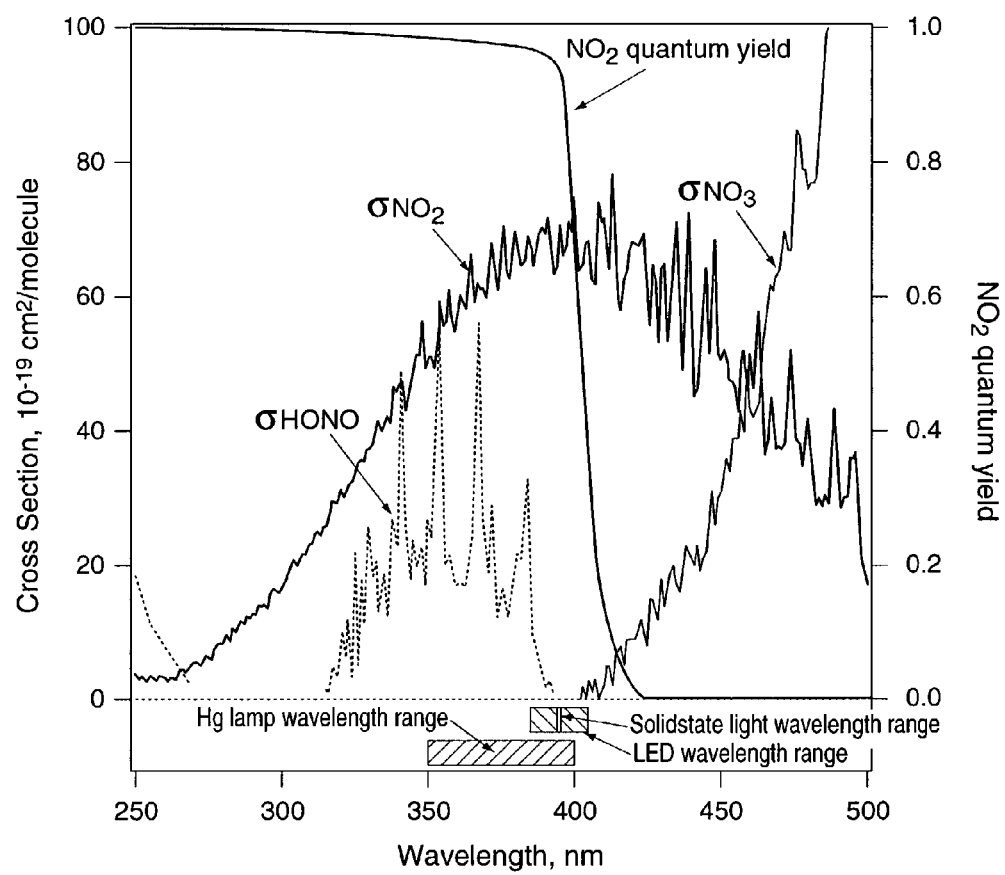
FIG. 9 illustrates the absorption cross-section data presented as a function of wavelength for $NO_2$ and for potential interferences in broadband photodissociation-chemiluminescence measurement.

FIG. 9 illustrates in chart form the absorption cross-section data presented as a function of wavelength for $NO_2$ and for potential interferences in broadband photodissociation-based measurement. Photodissociation means the removal of one or more atoms from a molecule by the absorption of a quantum of electromagnetic energy. This chart shows the absorption cross sections for $NO_2$, HONO, and $NO_3$, as well as the photolysis quantum yield for $NO_2$. On the bottom of the chart the spectral output ranges for the diode laser (solid line) and LED (hatched line) systems and a filtered Hg arc lamp are shown. The wavelength range of the solid state light sources (laser or LED; 385–405 nm) is optimally situated at the overlap of high $NO_2$ absorption and quantum yield, while having minimal overlap with the absorption cross sections of HONO and $NO_3$, both potential interferent species. Since there is no emission from the solid state light sources at longer wavelengths (unlike the Hg-arc lamp source) there is no interference from thermally sensitive species (e.g.—peroxyacetyl nitrate (PAN)).

Figure 10:
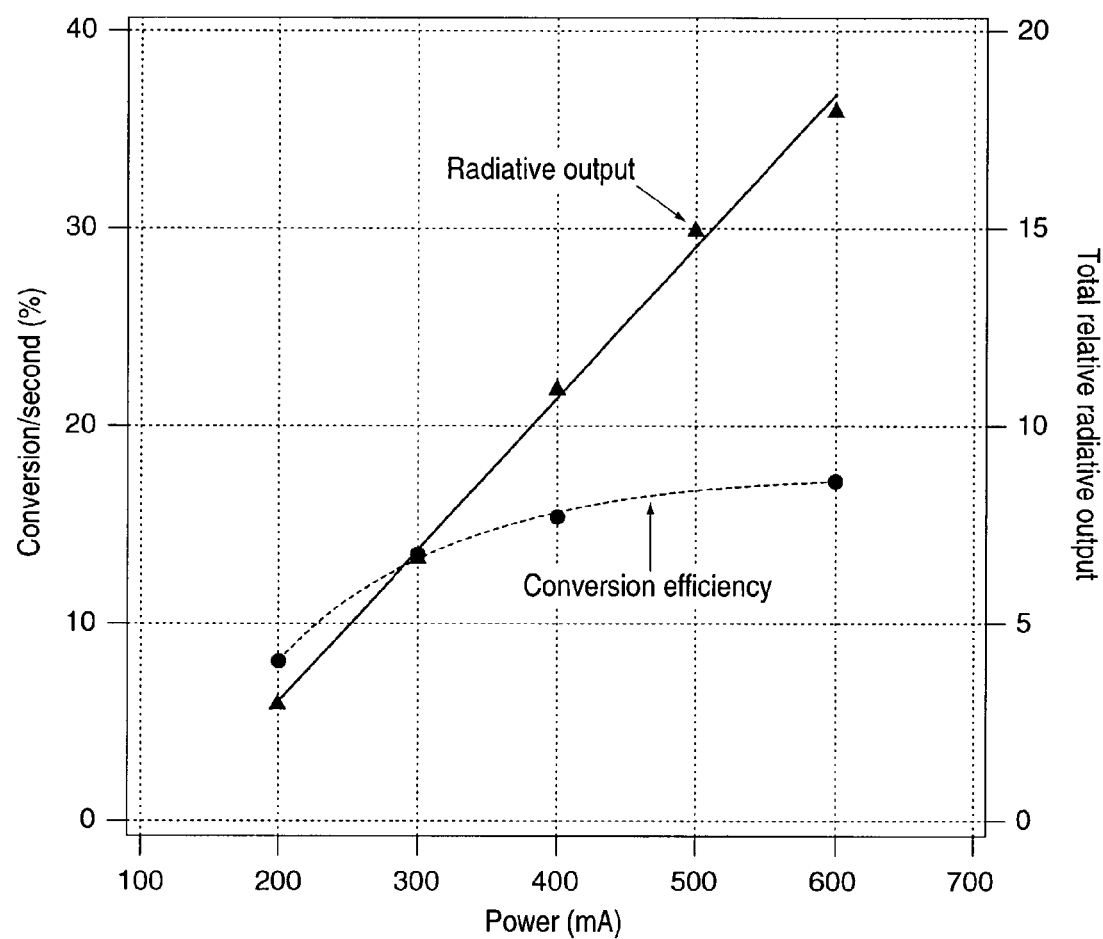
FIG. 10 illustrates the conversion efficiency and relative outputs achieved using one LED module in one embodiment of the solid-state light source photolytic nitrogen dioxide converter.

FIG. 10 illustrates the conversion efficiency and relative outputs achieved using one LED module in one embodiment of the solid-state light source photolytic nitrogen dioxide converter. This chart shows the conversion efficiency and relative radiative output achieved using one LED module in one embodiment of the invention as a function of power applied to the module. The performance in terms of conversion efficiency shows about 17% conversion per second at 600 mA applied power. The linear nature of the relative radiant output suggests that the LED is heating up with increasing power, resulting in a shift of the output radiation to wavelengths longer than 400 nm. The preferred embodiment of the invention employs two LED modules operated at 700 mA each and results in conversion efficiencies on the order of 65% per second. The non-linear increase in conversion efficiency going from one to two modules resulted from a coincident improvement in the flow dynamics of the photolysis chamber.

In Table 1 are reference for the performance characteristics of the solid-state light source photolytic converters and those described in prior art.

TABLE 1

| UV Light Source | Conversion Efficiency Demonstrated | Power Required | Estimated Light Source Lifetime | Efficiency[1] | Efficiency[2] |
|---|---|---|---|---|---|
| 395 nm LED arrays | 65%/sec. | 30 W | 5,000 hrs | .02 | 10 |
| 395 nm diode laser | 12%/sec. | 100 mW | 10,000 hrs | 1.2 | 2 |
| 200 W Hg lamp | 70%/sec. | 200 W | 200 hrs | .004 | 1 |
| 300 W Xe lamp | 18%/sec. | 300 W | 1,500 hrs | .0006 | 2 |

[1] In terms of power consumption (% conversion per watt)
[2] In terms of operating cost (hours of continuous operation per dollar for light source.

EXAMPLE 1

Dual LED Module Converter

A solid-state light source photolytic nitrogen dioxide converter 100 was constructed according to FIG. 1. This example includes two commercially available LED modules 122 and 132 (Roithner Lasertechnik, Austria) that each include 60 low power LED die. The modules are powered using a small AC-DC power supply 232 (Acopian Inc, Pennsylvania). In operation the LED modules 122 and 132 generate heat that must be dissipated. This is accomplished by mounting the modules to high-efficiency, forced-air heat sinks 104 and 110 (Cool Innovations, Inc, Canada). Thus configured, the LED modules 122 and 132 are mounted to an aluminum body 102 that contains of the diffuse-reflective, Teflon™-based material reflective material 116 (GigaHertz Optik, Germany). The reaction chamber 120 is formed by a cylindrical bore through the reflective material 116. The wall thickness of the reaction chamber 120 is designed to be about 1 cm, the minimum thickness needed to achieve the 98% reflectivity of the reaction chamber 120. The air sample is admitted to the reaction chamber 120 through a inlet piping 142 comprising NPT-pipe fitting (Swagelok, USA) mounted in the reflective material 116 orthogonal to the axis of the reaction chamber 120 and the LED modules 122 and 132. The air sample exits at an identical outlet piping 144 on the other end of the reaction chamber 120. The volume of the reaction chamber 120 is designed to be 17 milliliters (mL), which affords a 1 second residence time at a flow of 1 standard liter per minute (slpm). In operation, the air sample can be routed through external valving either through the reaction chamber 120 or through a non-illuminated volume of comparable volume. In both cases the outlet piping 144 is directed to a NO analyzer (usually a $NO/O_3$ chemiluminescence instrument). When the contents of the reaction chamber 120 are directed to the chemiluminescence analyzer the resultant signal is proportional to the concentration of NO plus $NO_2$ ($NO_x$). When the contents of the non-illuminated reaction chamber 120 are directed to the chemiluminescence analyzer the resultant signal is proportional to the concentration of NO. The difference between the two signals is proportional to the concentration of $NO_2$ in the sample.

Tests of the invention using two LED modules 122 and 132 operated at approximately 700 mA each show a conversion efficiency of 65%/second. This rate of conversion compares favorably with the best performance recorded using a broadband light source that is considerably more complex and expensive (Ryerson et al, 2000.) A summary of the operating characteristics of this invention and other photolytic conversion methods is shown in Table 1 above. It is clear from the data presented in Table 1 that the LED array embodiment of this invention offers comparable performance to the best of the broadband sources at marked improvement of efficiency in terms of both power consumption and operating costs. Another possible operational use of the configuration described would be to use an electronic relay to turn the power to the LED modules 122 and 132 on and off. The resultant signal would appear the same as that described above with alternate measurement of NOx and NO from the NO analyzer. Yet another possibility would be to use two independent NO analyzers to provide continuous measurements of both NO and NOx concentration, and thereby a continuous measurement of $NO_2$ concentration.

EXAMPLE 2

Diode Laser $NO_2$ Converter

A solid-state light source photolytic nitrogen dioxide converter 200 was constructed according to FIG. 2. The solid-state light source photolytic nitrogen dioxide converter 200 uses a commercially-packaged diode laser 202 emitting at 395 nm, with 25 mW of radiant output and beam dimensions of approximately 3×6 mm. The reaction tubes 204 and 206 designed to be used with the diode laser 202 consisted of 4 12-inch long glass tubes with an inner diameter of 5 mm, giving a total internal volume of about 17 mL (nominally a one second residence time at 1 liter per minute flow). The reaction tubes were joined together using Teflon™-coated aluminum blocks which had appropriate ports and channels milled into the block 214. The gas seal was formed by the glass prisms 208 used to direct the beam sequentially down each pipe, which were seated on o-rings on the block 214. A schematic diagram of this embodiment is shown in FIG. 2. The resultant $NO_2$ conversion efficiency was measured to be about 10% per second. This example works with essentially the same photolytic efficiency as a typical 300 W xenon lamp, using about 10,000 times less power. This is possible because all of the incident radiation is in a useful wavelength region and the photolysis cell design allowed for intimate joining of the light and gas paths. To achieve the desired >80% photolytic conversion efficiency using this example of the solid-state light source photolytic nitrogen dioxide converter either a single, more powerful diode laser 202, or multiple lower powered lasers may be employed.

Although there has been described what is at present considered to be the preferred embodiments of the present invention, it will be understood that the invention can be embodied in other specific forms without departing from the spirit or essential characteristics thereof. The preferred embodiment of the invention uses an LED module or diode laser as the UV light source and a diffuse-reflective photolysis cell. Within those bounds there are a number of possible configurations and operating parameters that can be used successfully. It is expected that many variations on the solid-state light source and photolysis cell material and geometry are possible.

In connection with the light source it is reasonable to fabricate a custom LED module that uses one or more LED die, of higher power than those currently employed, in a thermally optimized module that could produce one watt or more of usable UV irradiance. Such a module could provide near unit conversion of $NO_2$ to NO on time scales suitable for eddy-correlated measurements (approximately 10 Hz). Another possible embodiment of this invention could use one or more diode-lasers emitting at wavelengths between 350 and 420 nm mounted in a module similar to the LED die to accomplish the photolysis. The diode laser could be operated without attendant optics because of the highly reflective nature of the invented photolysis cell. In the case of both the LED-based module and the diode-laser-based module, thermal electric cooling could be used to increase both radiant output and lifetime of the source.

Another possible embodiment would be to use a similar arrangement of solid-state light source and diffuse-reflective reaction chamber with the light source wavelength selected for photolysis of a photo-reactive species other than $NO_2$. There are several possibilities where this technology could be used to solve difficult measurement problems, including measurement of nitrate radical ($NO_3$), formaldehyde (HCHO), and other aldehydes (e.g.—acetaldehyde). The nitrate radical could be selectively photolyzed using this method at wavelengths greater than 420, resulting in production of NO that could be subsequently measured using an NO instrument (chemiluminescence or LIF as described above). Formaldehyde and the high aldehydes could be photolyzed using this method at wavelengths greater than 320 nm, resulting in production of CO (carbon monoxide) that could subsequently be measured using one of several methods commonly known to those skilled in the art (e.g.— vacuum UV resonance fluorescence). Solid-state light sources similar to those describer earlier are available in appropriate wavelength ranges for these applications.

Variations on the photolysis cell geometry and material may be made to accommodate other desired cell residence times or operation at other than 1 atmosphere pressure. Reflective material other than the Teflon™-based material used here may work as well. These could include barium sulfate coated on the outside of a glass cell as an alternative diffuse reflector, or aluminum, silver, or other materials as an alternative specular reflector. The present embodiments are, therefore, to be considered in all aspects as illustrative and not restrictive. The scope of the invention is indicated by the appended claims rather than the foregoing description.

What is claimed is:

1. A photolytic $NO_2$ converter for converting $NO_2$ present in a gas sample into NO, comprising:

a body including a reaction chamber that possesses diffuse reflective properties located substantially within said body, said reaction chamber possessing at least one aperture, said reaction chamber being highly reflective, having a reflective efficiency of at least 0.95 for light in the ultraviolet wavelength range;

a reaction chamber inlet in communication with said reaction chamber for transporting a gas sample into said reaction chamber;

a reaction chamber outlet in communication with said reaction chamber for transmitting a processed gas sample out of said reaction chamber; and at least one low-power light-emitting diode (LED) configured to produce UV wavelength radiation in the range of 350–420 nm optimally situated at the overlap of high $NO_2$ adsorption and quantum yield located substantially adjacent to said at least one aperture to enable UV wavelength radiation to pass from said at least one low-power LED into said reaction chamber through said at least one aperture, for converting $NO_2$ present in a gas sample transported into said reaction chamber by said reaction chamber inlet into NO in a processed gas sample for transportation out of said reaction chamber by said reaction chamber outlet, said reaction chamber having a volume for providing a residence time of said processed gas sample in said reaction chamber of less than 5 seconds.

2. The photolytic $NO_2$ converter as in claim 1, further comprising:

NO detector means, in communication with said reaction chamber outlet, for generating a signal indicative of a concentration of NO in said processed gas sample.

3. The photolytic $NO_2$ converter as in claim 1, further comprising:

at least one heat sink mounted to said body and located substantially near said at least one low-power LED.

4. The photolytic $NO_2$ converter as in claim 1, further comprising:

at least one thermoelectric cooling device mounted to said body and located substantially near said at least one low-power LED.

5. The photolytic $NO_2$ converter as in claim 1, wherein said diffuse reflective properties are produced by a material selected from the group consisting of materials and Barium Sulfate polytetrafluoroethylene (Teflon).

6. The photolytic $NO_2$ converter as in claim 1, further comprising:

a means for controllably introducing the gas sample to the reaction chamber, said reaction chamber, and said means for controllably introducing said gas sample to the reaction chamber, each comprises a volume which minimizes a residence time of the gas sample in said photolytic $NO_2$ converter.

7. A photolytic $NO_2$ converter for converting $NO_2$ present in a gas sample into NO, comprising:

a body including a reaction chamber that possesses diffuse reflective properties by a polytetrafluoroethylene (Teflon) material, said reaction chamber located substantially within said body and possessing at least one aperture, said reaction chamber having a reflective efficiency of at least 0.95 for light in the ultraviolet wavelength range;

a reaction chamber inlet in communication with said reaction chamber for transporting a gas sample into said reaction chamber, a reaction chamber outlet in communication with said reaction chamber for transmitting a processed gas sample out of said reaction chamber; and at least one light-emitting diode (LED) configured to produce UV wavelength radiation in the range of 350–420 nm optimally situated at the overlap of high $NO_2$ adsorption and quantum yield, located substantially adjacent to said at least one aperture to enable UV wavelength radiation to pass from said at least one LED into said reaction chamber through said at least one aperture, for converting $NO_2$ present in a gas sample transported into said reaction chamber by said reaction chamber inlet into NO in a processed gas sample for transportation out of said reaction chamber by said reaction chamber outlet, said reaction chamber having a volume for providing a residence time of said processed gas sample in said reaction chamber of less than 2 seconds.

* * * * *